United States Patent
Orsak

(10) Patent No.: US 10,213,241 B2
(45) Date of Patent: Feb. 26, 2019

(54) METHOD AND DEVICE FOR INSERTION OF ORTHOPEDIC FIXATION PIN WITH BLIND HOLE

(71) Applicant: Wright Medical Technology, Inc., Memphis, TN (US)

(72) Inventor: James Edward Orsak, Eads, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 15/707,116

(22) Filed: Sep. 18, 2017

(65) Prior Publication Data

US 2018/0000530 A1    Jan. 4, 2018

Related U.S. Application Data

(63) Continuation of application No. 12/946,269, filed on Nov. 15, 2010, now Pat. No. 9,763,720.

(60) Provisional application No. 61/261,928, filed on Nov. 17, 2009.

(51) Int. Cl.
| | |
|---|---|
| *A61B 17/86* | (2006.01) |
| *A61B 17/16* | (2006.01) |
| *A61B 17/88* | (2006.01) |

(52) U.S. Cl.
CPC ........ *A61B 17/864* (2013.01); *A61B 17/1615* (2013.01); *A61B 17/1682* (2013.01); *A61B 17/8897* (2013.01)

(58) Field of Classification Search
CPC .............. A61B 17/864; A61B 17/1615; A61B 17/1682

See application file for complete search history.

(56) References Cited

U.S. PATENT DOCUMENTS

| | | | |
|---|---|---|---|
| 5,334,204 A | 8/1994 | Clewett et al. | |
| 5,366,374 A | 11/1994 | Vlassis | |
| 5,643,269 A | 7/1997 | Harle | |
| 6,312,432 B1 | 11/2001 | Leppelmeier | |
| 6,325,583 B1 | 12/2001 | Mattle et al. | |
| 6,503,252 B2 | 1/2003 | Hansson | |
| 7,354,442 B2 | 4/2008 | Sasso et al. | |
| 7,637,929 B2 | 12/2009 | Auth | |
| 2004/0006345 A1 | 1/2004 | Vlahos et al. | |
| 2004/0101381 A1 | 5/2004 | Kram et al. | |
| 2004/0172022 A1 | 9/2004 | Landry et al. | |
| 2006/0078847 A1 | 4/2006 | Kwan | |
| 2007/0025827 A1 | 2/2007 | Pryor | |
| 2009/0198237 A1* | 8/2009 | Downey | ............ A61B 17/7098 606/62 |
| 2013/0190817 A1* | 7/2013 | Bouduban | .......... A61B 17/0401 606/232 |

* cited by examiner

*Primary Examiner* — Christian Sevilla
(74) *Attorney, Agent, or Firm* — Duane Morris LLP

(57) ABSTRACT

A fixation device is disclosed including an elongate body extending from a distal end to a proximal end. The distal end defines a blind hole having a diameter and extending to a depth from a distal tip. The diameter of the blind hole is sufficient to receive a k-wire therein.

10 Claims, 11 Drawing Sheets

METHOD AND DEVICE FOR INSERTION OF ORTHOPEDIC FIXATION PIN WITH BLIND HOLE

CROSS-REFERENCE TO RELATED APPLICATIONS

This application is a continuation of U.S. application Ser. No. 12/946,269 filed Nov. 15, 2010, which claims priority to U.S. provisional patent application No. 61/261,928 filed on Nov. 17, 2009, the entirety of which are incorporated herein by reference.

SUMMARY

A fixation device is disclosed including an elongate body extending from a distal end to a proximal end. The distal end defines a blind hole having a diameter and extending to a depth from a distal tip. The diameter of the blind hole is sufficient to receive a k-wire.

A method is also disclosed in which a k-wire is inserted into a bone such that a portion of the k-wire extends from a surface of the bone. A fixation device that defines a blind hole is slid over a portion of the k-wire that extends from a surface of the bone. The fixation device is driven into the bone along an axis defined by the k-wire. A bottom wall of the fixation device contacts an end of the k-wire as the fixation device is driven into the bone. The k-wire is removed from the bone.

The foregoing and other aspects will be apparent from the following description of the preferred embodiments. In the description, reference is made to the accompanying drawings which form a part hereof, and in which there is shown by way of illustration, and not limitation, a preferred embodiment. Such embodiment does not necessarily represent the full scope of the invention, and reference must therefore be made to the claims herein for interpreting the scope of the invention and its equivalents.

BRIEF DESCRIPTION OF THE DRAWINGS

These and other features and advantages of the present invention will be more fully disclosed in, or rendered obvious by the following detailed description of the preferred embodiments of the invention, which are to be considered together with the accompanying drawings wherein like numbers refer to like parts and further wherein.

DETAILED DESCRIPTION

Figure 1:
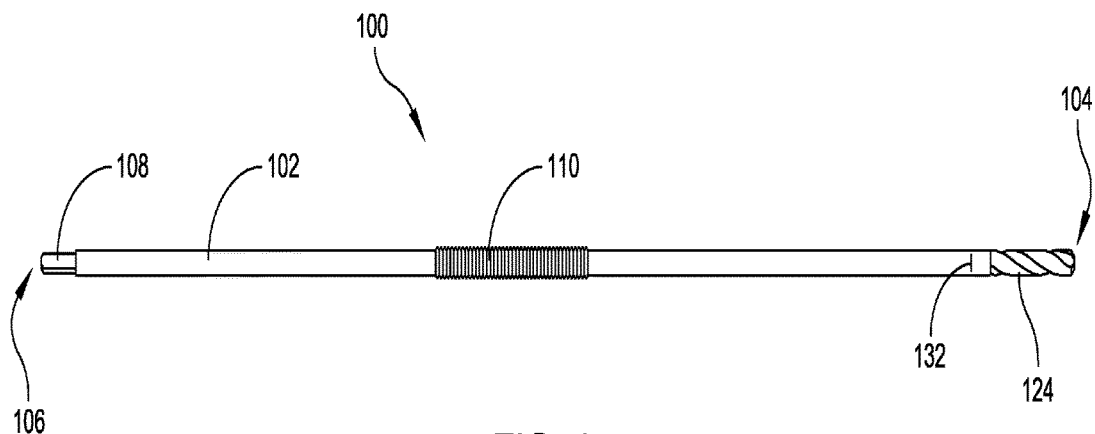
FIG. 1 is a side view of one example of a fixation device.

This description of preferred embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

FIGS. 1-4 illustrate one example of an improved fixation device 100. The fixation device 100 may be a transfixion pin, a half-pin for coupling to other components of an external fixator, a traction pin, or the like. As shown in FIG. 1, fixation device 100 includes an elongate body 102 having a distal end 104 and a proximal end 106. Proximal end 106 of the fixation device may include an engagement feature 108 for engagement with a driving device. Threads 110 may be optionally disposed along a portion of a length of fixation device 100 between distal end 104 and proximal end 106.

Figure 3:
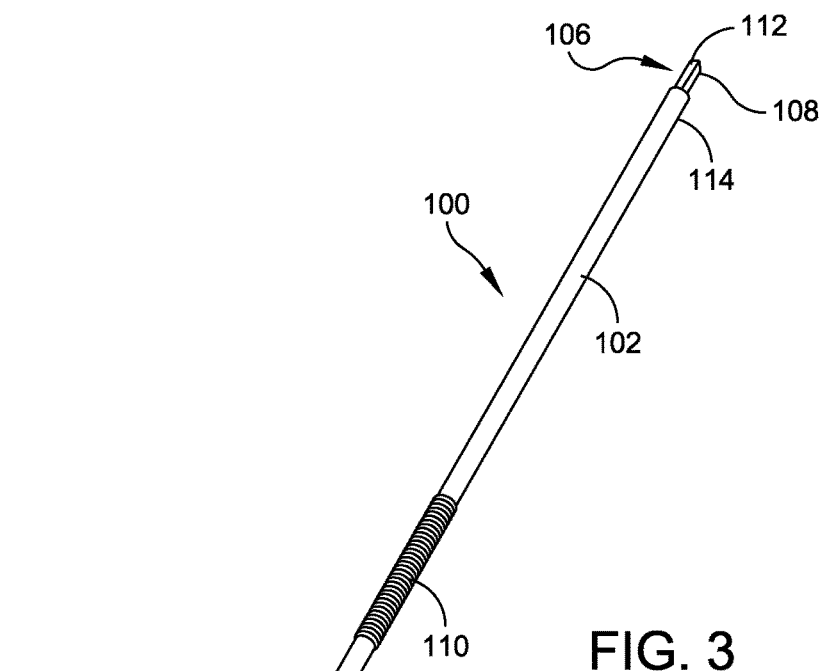
FIG. 3 is an isometric view of the fixation device illustrated in FIG. 1.

Engagement feature 108 of proximal end 106 may take a variety of forms. As best seen in FIG. 3, engagement feature 108 includes a plurality of flats 112 formed on an exterior surface 114 of elongate body 102 so as to provide a gripping surface for a driving device. As will be understood by one skilled in the art, the number of flats 112 on exterior surface 114 of proximal end 106 may be varied such that proximal end 106 may have a variety of cross-sectional geometries including, but not limited to, triangular, square, pentagonal, hexagonal, to name a few. In some embodiments, engagement feature 108 formed at proximal end 106 of fixation device 100 may be a socket-type engagement feature such as, for example, a hex socket for receiving a hex key. Other examples of other socket-type engagement features include, but are not limited to, a Phillips socket, a Torx socket, a Spanner head, a poly-drive, or the like.

Figure 2:
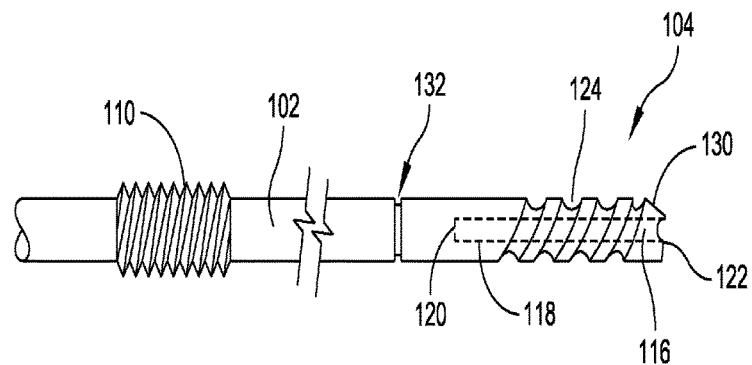
FIG. 2 is a detailed side view of a portion of the fixation device shown in FIG. 1.

As best seen in FIGS. 2 and 3, distal end 104 of fixation device 100 defines a blind hole 116 having a side wall 118 and a bottom wall 120. Blind hole 116 may be formed such that it is concentric with an outer diameter of elongate body 102 and extends along a central axis defined by elongate body 102. Blind hole 116 may have a diameter that is sufficiently large to receive a k-wire. The engagement between blind hole 116 and the k-wire may be a slip-fit engagement. In some embodiments, blind hole 116 has a diameter between approximately 1 mm (approximately 0.04 inches) to approximately 3 mm (approximately 0.12 inches). One skilled in the art will understand that the diameter of blind hole 116 may be adjusted to accommodate k-wires of different diameters. In some embodiments, blind hole 116 may extend to a depth of approximately 2.5 cm (approximately 1 inch) and 5 cm (approximately 2 inches). The depth of blind hole 116, i.e., the distance from a distal tip 122 of the fixation device 100 to bottom wall 120, may be vary. However, in some embodiments an overly shallow depth, e.g., less than 1 mm, may cause some difficulty for the user to engage and align the k-wire with blind hole 116. In contrast, overly deep depth of blind hole 116 may result in side and bottom walls 118, 120 of blind hole 116 being difficult to sterilize as well as reducing the strength of fixation device 100.

Figure 4:
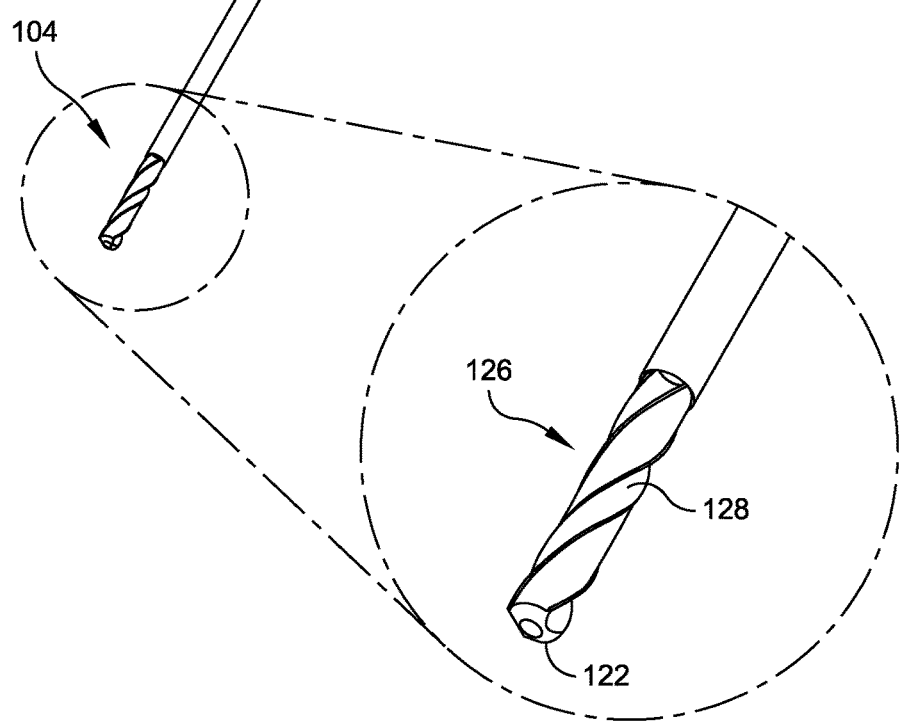
FIG. 4 is a detail view of the distal end of the fixation device shown in FIG. 3.

Distal end 104 may also include a cutting feature 124 for drilling and securing fixation device 100 into a bone. For example, distal end 104 may include threads, a fluted shank, or another feature to aide in the insertion of fixation device 100 into bone. In FIG. 4, distal end 104 of the fixation device 100 is shown with a fluted shank 126, which may include one or more helical grooves 128 defined by body 102 of fixation device 100 to form a twist drill as will be understood by one skilled in the art. Distal tip 122 of fixation device 100 may also include a taper 130 to aide in the placement of fixation device 100 within bone as illustrated in FIG. 2.

Threads 110 may be disposed at various positions along the length of elongate body 102 of fixation device 100 for engaging bone to maintain the position of fixation device 100 in bone. In one embodiment, threads 110 are disposed approximately halfway between distal end 104 and proximal end 106 and may be sufficiently long to extend beyond either side of the bone into which fixation device 100 is located.

Fixation device 100 may also include a cutting guide 132 disposed along a length of body 102 for identifying a location at which blind hole 116 ends. In some embodiments, cutting guide 132 is a line etched into an outer surface 134 of fixation device 100 and is disposed adjacent to fluted shank 126, as seen in FIGS. 1 and 2. Cutting guide 132 may be a line that completely, or partially, encircles elongate body 102 of fixation device 100. One skilled in the art will understand that cutting guide 132 may take a variety of other forms including, but not limited to, a crimp, a bump, texturing, coloring, or the like.

Bone Screw

Figure 5:
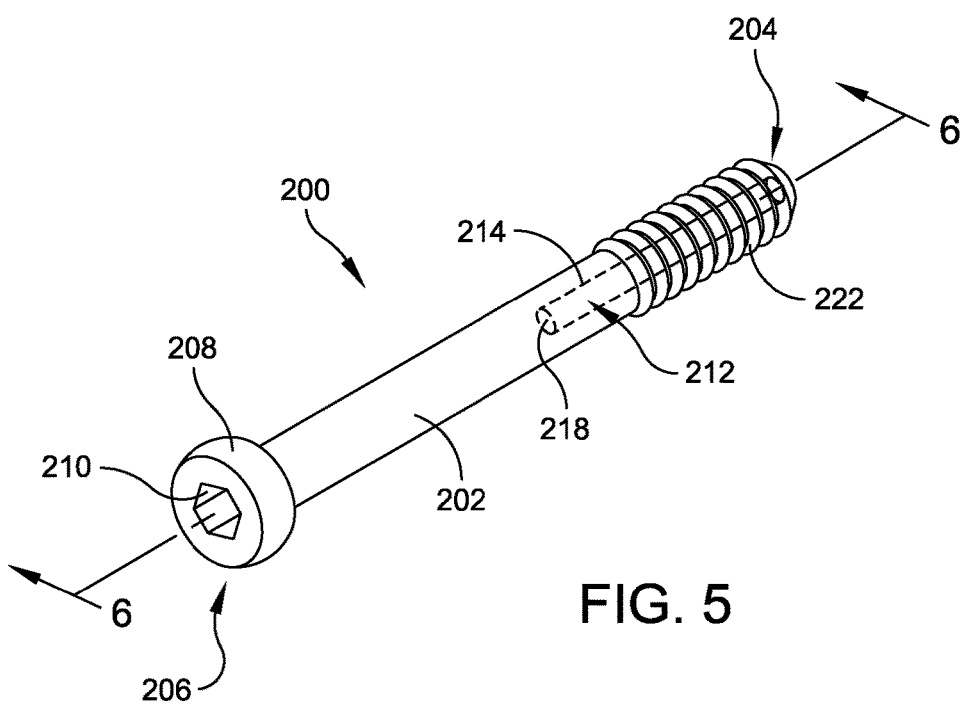
FIG. 5 is an isometric view of another example of a fixation device.
Figure 6:
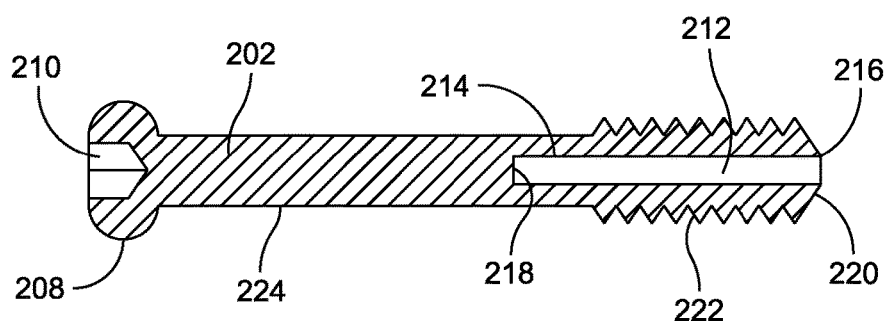
FIG. 6 is a sectional view of the fixation device taken along line 6-6 in FIG. 5.

FIGS. 5-6 illustrate one example of an improved fixation device 200 configured as a bone screw. As shown in FIG. 5, fixation device 200 includes a completely or partially threaded elongate body 202 having a distal end 204 and a proximal end 206. Proximal end 206 may have an enlarged diameter forming a head 208, which defines an engagement feature 210. For example, head 208 may define an engagement socket 210 configured to engage a driving tool such as, for example, a Phillips screwdriver, a hex or Allan key, a Torx driver, or the like for driving fixation device 200 into bone as described below.

Distal end 204 of bone screw 200 defines a blind hole 212 having a side wall 214 extending from a distal tip 216 to a bottom wall 218 as best seen in FIG. 6. The depth of blind hole 212 may be approximately 2.5 cm (approximately 1 inch) to approximately 5 cm (approximately 2 inches) although one skilled in the art will understand that the depth of blind hole 212 may be vary. Distal tip 216 may include a taper 220 to aide in the insertion of fixation device 200 in bone.

Threads 222 may extend along an exterior surface 224 of elongate body 202 from distal tip 216 towards proximal end 206. However, one skilled in the art will understand that threads 222 may be disposed at various positions along the elongate body.

The fixation devices 100, 200 described above may be fabricated from any medical grade material including, but not limited to, stainless steel, titanium, a cobalt chrome alloy, to name a few. Additionally, the fixation devices may be provided a wide-range of sizes and styles as will be understood by one skilled in the art.

Surgical Procedures

I. Installation of External Fixation Pin in Neck of Talus

Figure 7:
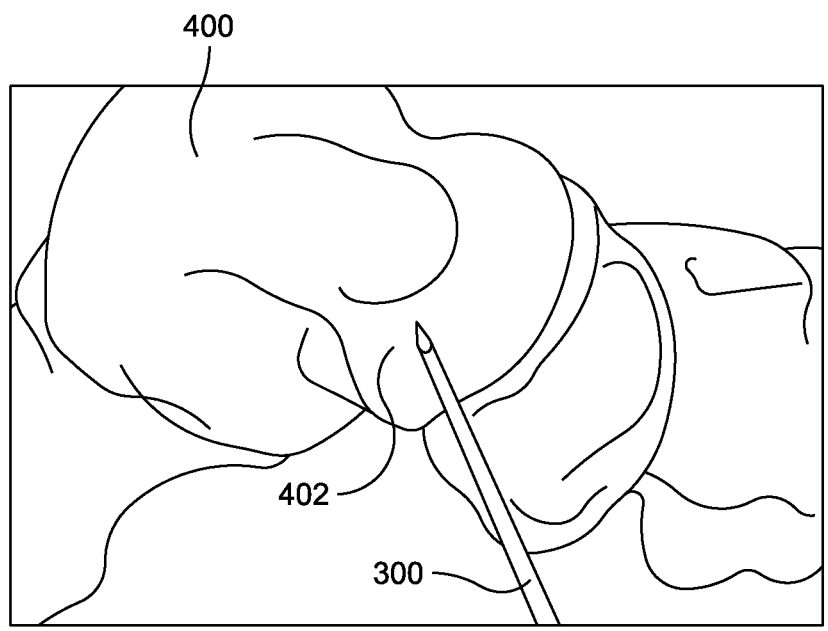
FIG. 7 illustrates a k-wire being inserted into a neck of a talus.
Figure 8:
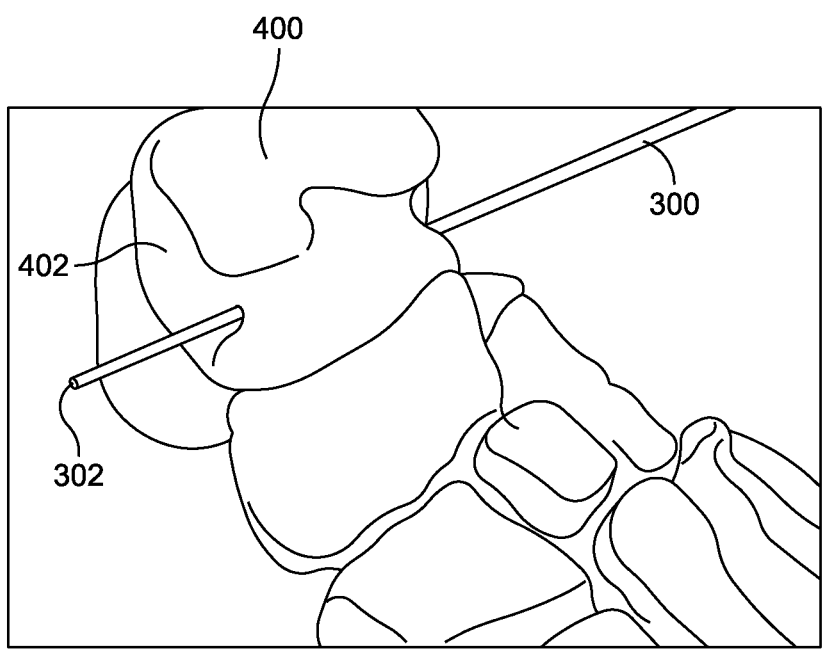
FIG. 8 illustrates a k-wire inserted into the neck of the talus.

FIGS. 7-13 illustrate a fixation device 100 in the form of a fixation pin being inserted into a neck of a talus 400. As shown in FIGS. 7 and 8, a k-wire 300 may be inserted through a neck 402 of talus 400. A surgeon may check the alignment of k-wire 300 in talus 400 using fluoroscopy as will be understood by one skilled in the art. If the surgeon determines that k-wire 300 is not properly aligned, then k-wire 300 may be removed and repositioned within talus 400. Fluoroscopy may again be used to check the alignment of the k-wire 300.

Figure 9:
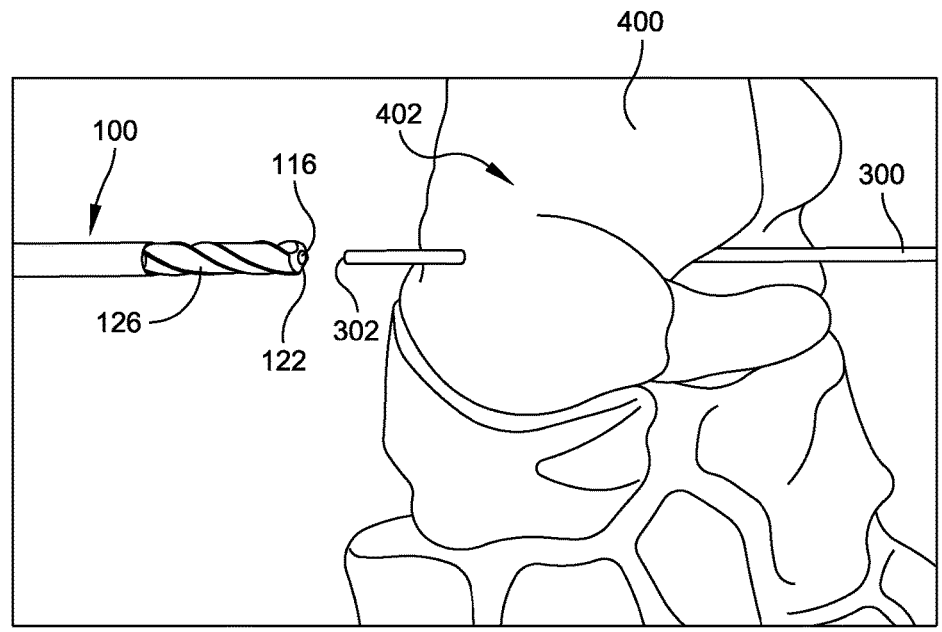
FIG. 9 illustrates a blind hole of a fixation device being aligned with an end of the k-wire inserted through the neck of the talus.
Figure 10:
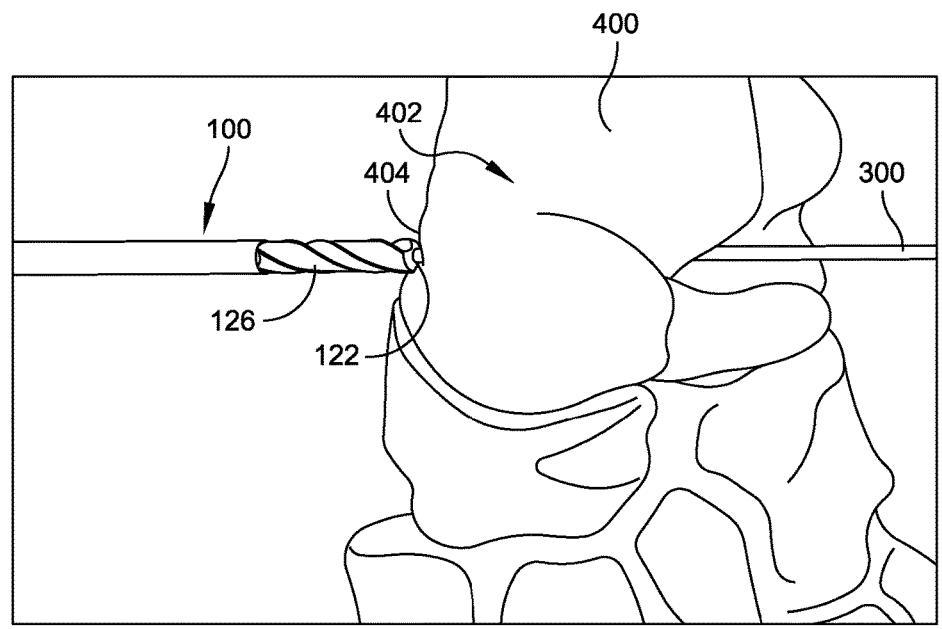
FIG. 10 illustrates a fixation device inserted over an end of the k-wire inserted through the neck of the talus.

Once k-wire 300 is positioned in talus 400, a fixation pin 100 may secured in neck 402 of talus 400. To secure fixation pin 100 in talus 400, blind hole 116 of fixation pin 100 is aligned with an end 302 of k-wire 300 (FIG. 9). Blind hole 116 is then slid over end 302 of k-wire 300 until distal tip 122 is brought into engagement with a surface 404 of talus 400 (FIG. 10). K-wire 300 may be positioned within talus 400 such that end 302 that is received within blind hole 116 of fixation pin 100 does not contact bottom wall 120 of blind hole 116 when distal tip 122 of fixation pin 100 contacts surface 404 of talus 400.

Figure 11:
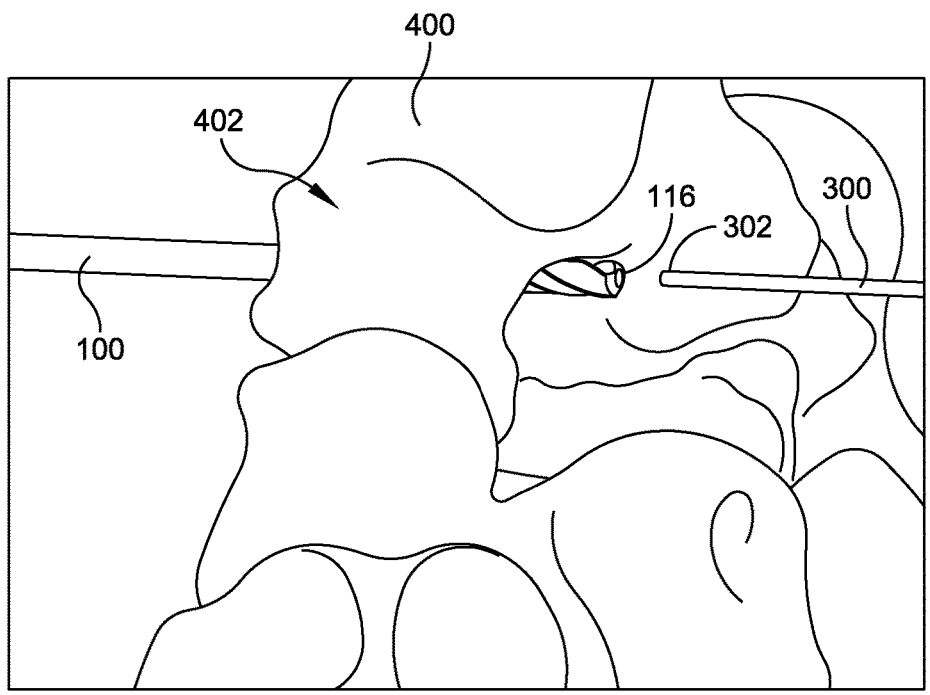
FIG. 11 illustrates a fixation device inserted through a neck of the talus.

The surgeon may use a tool, such as a Jacobs chuck or other device (not shown) for engaging engagement feature 108 of fixation pin 100, to drive fixation pin 100 into neck 402 of talus 400. For example, the surgeon may use the driving device to rotate fixation pin 100 causing fluted shank 126 of fixation pin 100 to cut into talus 400. As fixation device 100 advances into talus 400, bottom wall 120 of blind hole 116 contacts end 302 of k-wire 300 resulting in k-wire 300 being driven along with fixation pin 100 into talus 400. The surgeon continues to drive fixation pin 100 into talus 400 until k-wire 300 is forced from the opposite side of talus 400 (FIG. 11). In some procedures, the surgeon may continue to drive fixation pin 100 into talus 400 until one to two inches of elongate body 102 of fixation pin 100 are exposed on either side of talus 400. If fixation pin 100 includes threads 110 disposed along the length of body 102, then the surgeon may continue to drive fixation pin 100 into talus 400 until a portion of threads 110 are visible on either side of talus 400.

Figure 12:
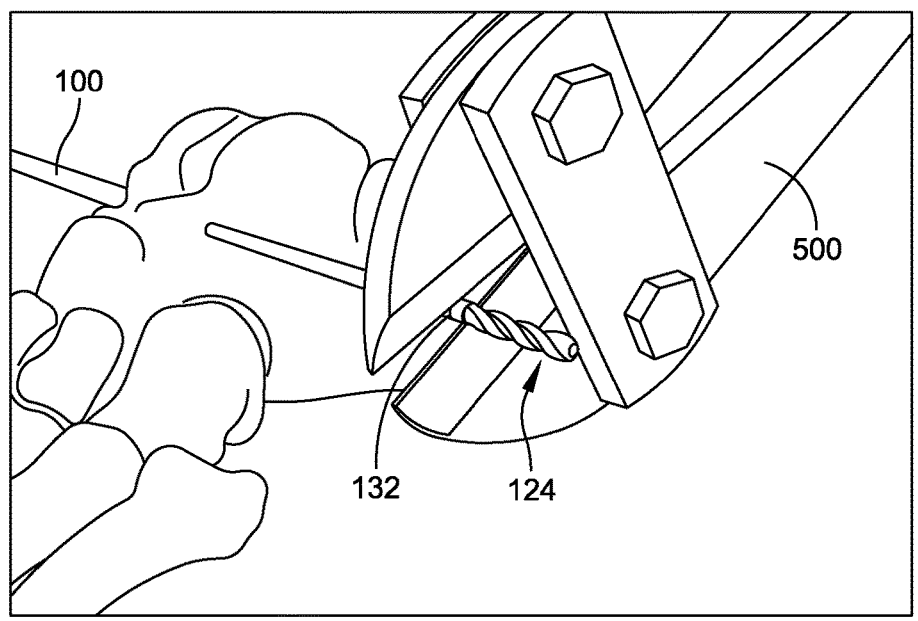
FIG. 12 illustrates a distal end of the fixation device being cut by a surgical tool.
Figure 13:
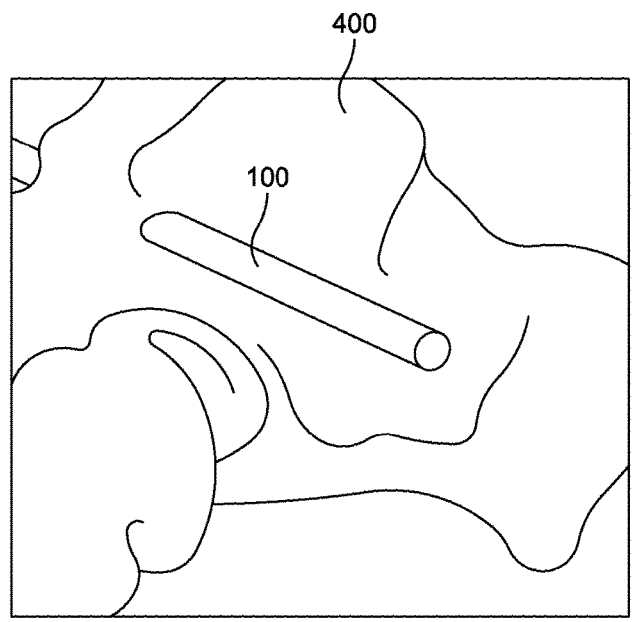
FIG. 13 illustrates the fixation device installed through the neck of the talus.

With the fixation pin 100 secured in neck 402 of talus 400, the surgeon may locate cutting guide 132 disposed along the length of fixation pin 100 and cut fixation pin 100 to a desired length (FIG. 12). For example, the surgeon may cut fixation pin 100 with cutters 500 such that fluted shank 126 and blind hole 116 at distal end 104 are removed to leave a solid fixation pin 100 disposed within talus 400 (FIG. 13). The surgeon may attach additional devices for maintaining the position of the ankle to fixation pin 100 as will be understood by one skilled in the art.

II. Installation of Bone Screw For Subtalar Fusion

Figure 14:
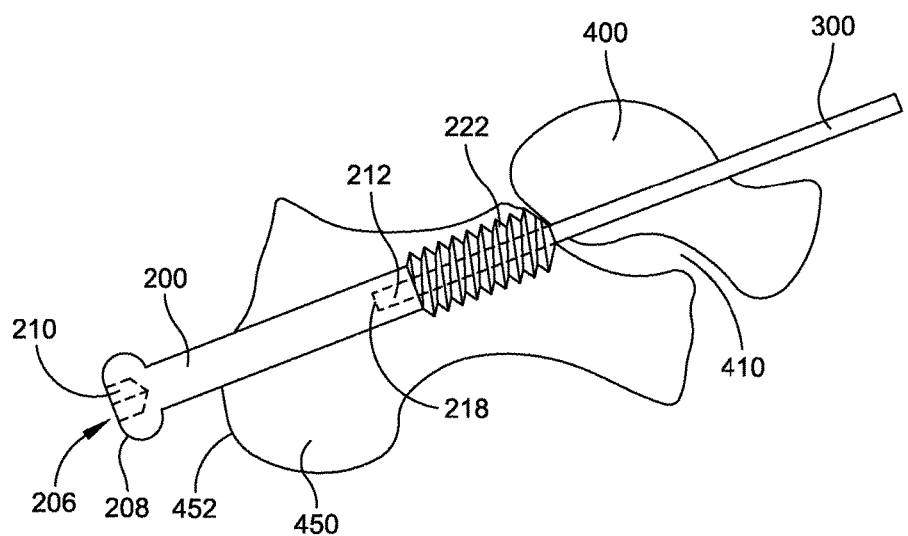
FIG. 14 illustrates a fixation device being installed across a subtalar joint.

The use of a bone screw fixation device 200 for fusing of subtalar joint 410 between a talus 400 and a calcaneus 450 is illustrated in FIG. 14. An ankle of a patient may be opened and a k-wire 300 inserted through an inferior portion of calcaneus 450 through talus 400. A surgeon may check the position of k-wire 300 in calcaneus 450 and talus 400 using fluoroscopy and reposition the k-wire 300 as desired. Once the desired positioning of k-wire 300 in calcaneus 450 and talus 400 is achieved, the surgeon may slide blind hole 212 disposed at distal end 204 of bone screw 200 over an end 302 of k-wire 300 until distal tip 216 of bone screw 200 contacts a surface 452 of calcaneus 450. As described above, k-wire 300 may extend from calcaneus 450 such that end 302 of k-wire 300 does not contact bottom wall 218 of blind hole 212 when distal tip 216 of bone screw 200 contacts surface 452 of calcaneus 450.

The surgeon may then use a driving tool such as an Allan key, Torx driver, screwdriver or other device configured to engage engagement feature 210 disposed on proximal end 206 of bone screw 200 to drive bone screw 200 into calcaneus 450, across subtalar joint 410, and into talus 400. Threads 222 disposed along elongate body 202 of bone screw 200 may grip talus 400, calcaneus 450, or both talus 400 and calcaneus 450 to fuse subtalar joint 410. K-wire 300 may then be removed when bone screw 200 is secured in calcaneus 450 and talus 400.

III. Installation of Bone Screw For Plateau Facture of Tibia

Figure 15:
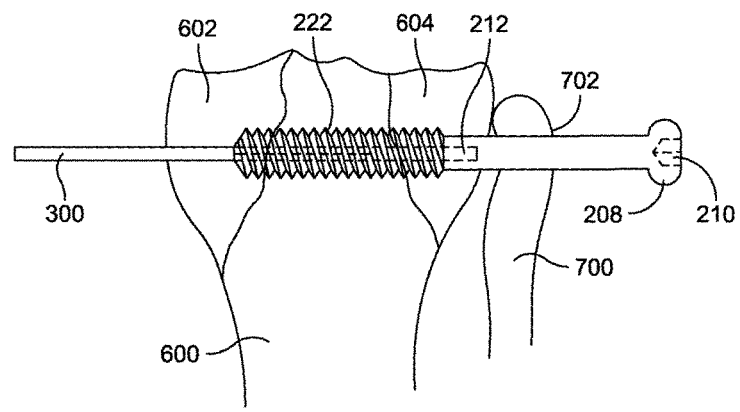
FIG. 15 illustrates a fixation device being installed across a fibula and a tibial platform to fuse a fracture of the tibial plateau.

FIG. 15 illustrates a bone screw fixation device 200 for correcting a fracture of a tibial plateau 600. A k-wire 300 may be inserted through fibula 700, bone segment 604, tibia 600, and bone segment 602. Once the surgeon is satisfied with the position of k-wire 300 in fibula 700, tibia 600, and bone segments 602, 604, a bone screw 200 is selected and blind hole 212 is slid over an end k-wire 300 until distal tip 216 of bone screw 200 contacts a surface 702 of fibula 700. As described above, k-wire 300 may extend from fibula 700 such that an end 302 of the k-wire 300 does not contact bottom wall 218 of blind hole 212 when distal tip 216 of bone screw 200 contacts surface 702 of fibula 700.

The surgeon may then drive bone screw 200 into fibula 700, first bone segment 604, tibia 600, and into second tibial bone segment 602 by using a tool such as an Allan key, Torx driver, or other device configured to engage engagement features 210-1, 210-2 disposed on proximal ends 206-1, 206-2 of bone screws 200-1, 200-2. K-wires 300 may be removed when threads 222-1, 222-2 of bone screws 200-1, 200-2 are secured in fibula 700, tibia 600 and bone segments 602, 604. Heads 208-1, 208-2 of bone screws 200-1, 200-2 retain bone segments 602, 604 against tibia 600 to promote fusion of the fractures.

IV. Installation of Bone Screw For Pilon Fracture of Tibia

Figure 16:
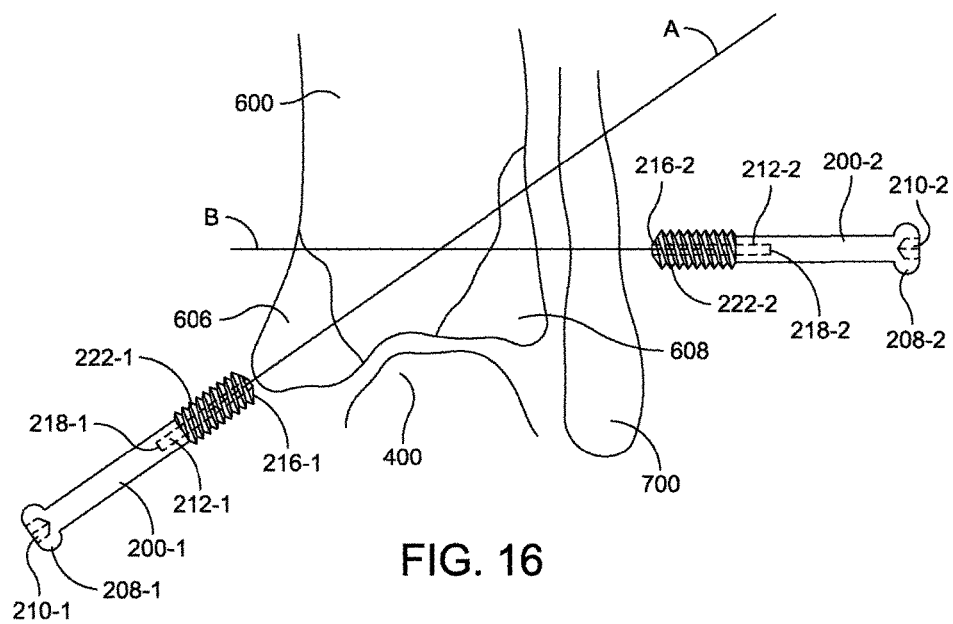
FIG. 16 illustrates a fixation device being installed across a fibula and a base of a tibia to fuse a fracture at the base of a tibia.

FIG. 16 illustrates a pair of bone screw fixation devices 200-1, 200-2 to correct a pilon fracture. A k-wire (not shown) may be inserted through a first tibial bone segment 606 and into the base of tibia 600 along the line A shown in FIG. 16. A second k-wire may be inserted through a second tibial bone segment 608 and into the base of tibia 600. Fewer or more k-wires may be used depending on the number of bone fragments as will be understood by one skilled in the art. A surgeon may check the position of the k-wires using fluoroscopy and reposition the k-wires until the desired position of the k-wires has been achieved as will be understood by one skilled in the art.

Blind holes 212-1, 212-2 of bone screw fixation devices 200-1, 200-2 may be inserted over the respective k-wires. The surgeon may secure bone segments 606, 608 to tibia 600 by driving bone screws 200-1, 200-2 into tibia 600. As bone screws 200-1, 200-2 are driven into the tibia, bottom walls 218-1, 218-2 of blind holes 212-1, 212-2 contact the ends of the k-wires forcing the k-wires in the direction of travel of the bone screw with which it is in contact. Bone screws 200-1, 200-2 may driven into tibia 600 until distal tip 216-1, 216-2 of each bone screw is close to a surface of tibia 600 and head 208-1, 208-2 of the bone screw contacts a surface of bone segment 606, 608 that the screw is securing to tibia 600. With bone screws 200-1, 200-2 secured to the tibia, the k-wires may be removed from tibia 600 by pulling the k-wires along the intramedullary channel that they formed by being inserted into tibia 600.

V. Charcot Foot

Figure 17:
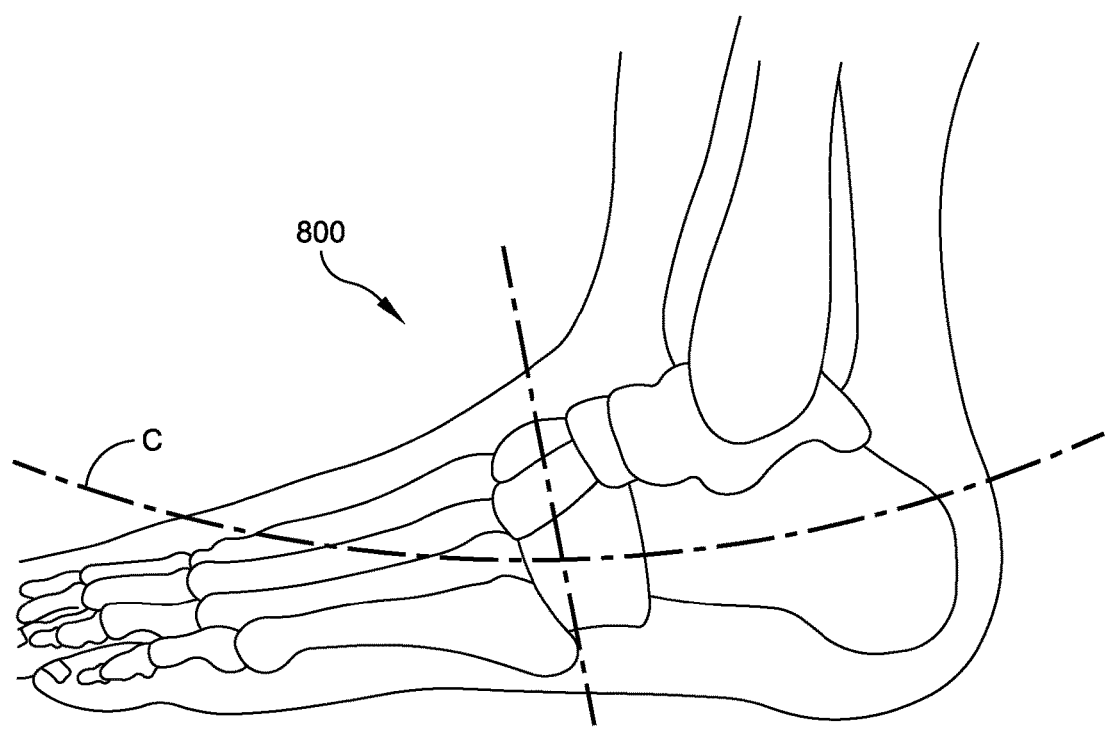
FIG. 17 is a medial view of a Charcot foot.
Figure 18:
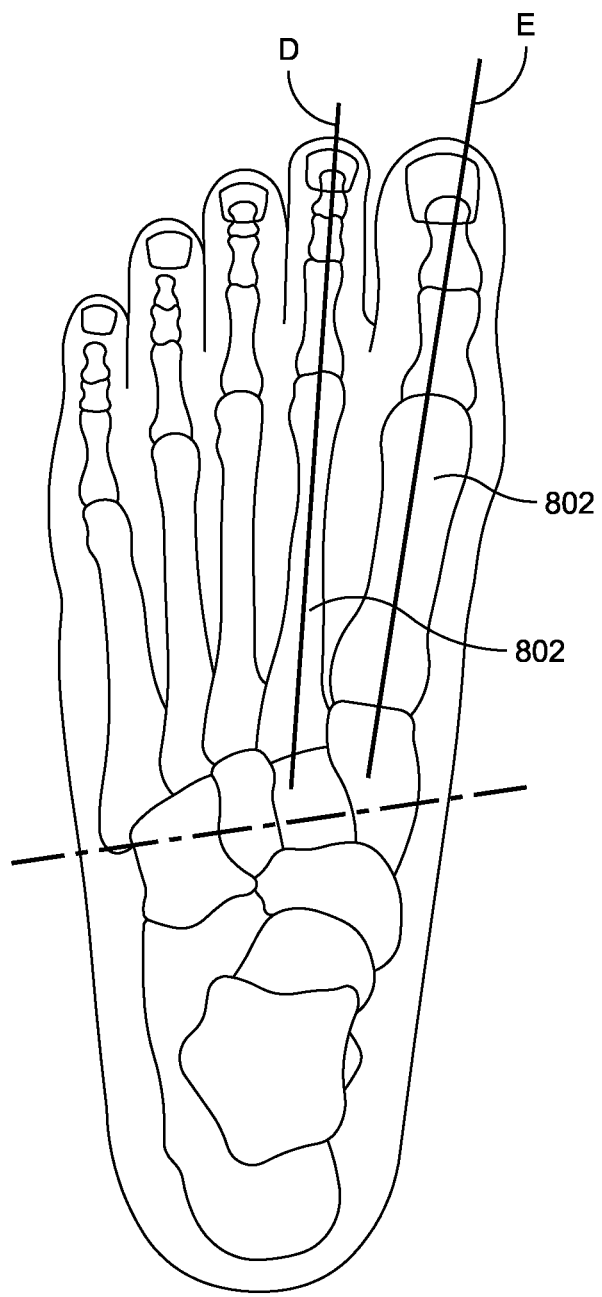
FIG. 18 illustrates the metatarsal axes along which k-wires are installed for a foot beaming operation.

Fixation devices 100, 200 may also be used in a beaming surgical procedure to correct a collapsed arch such as a Charcot foot. FIG. 17 illustrates a Charcot foot 800 having a collapsed arch as shown by line C. K-wires may be installed along the axes defined by the metatarsals as indicated by the lines D and E in FIG. 18. Bone screw fixation devices may then be inserted over k-wires 300 through metatarsals 802, cuneiforms 804, navicular 806, and into talus 400 to restore the arch of the mid-foot. A surgeon may check the positioning of the k-wires using fluoroscopy as will be understood by one skilled in the art.

When the desired positioning of the k-wires has been achieved, the surgeon may insert each bone screw 200 through the metatarsal 802, cuneiform 804, navicular 806, and into talus 400 using the k-wires as a guide. As described above, a blind hole 212 of a bone screw 200 is slid over a k-wire 300, which is used to guide the installation of the bone screw fixation device 200. A surgeon drives bone screw 200 into place using a tool configured to engage engagement feature 210 disposed on the proximal end of bone screw 200.

Figure 19:
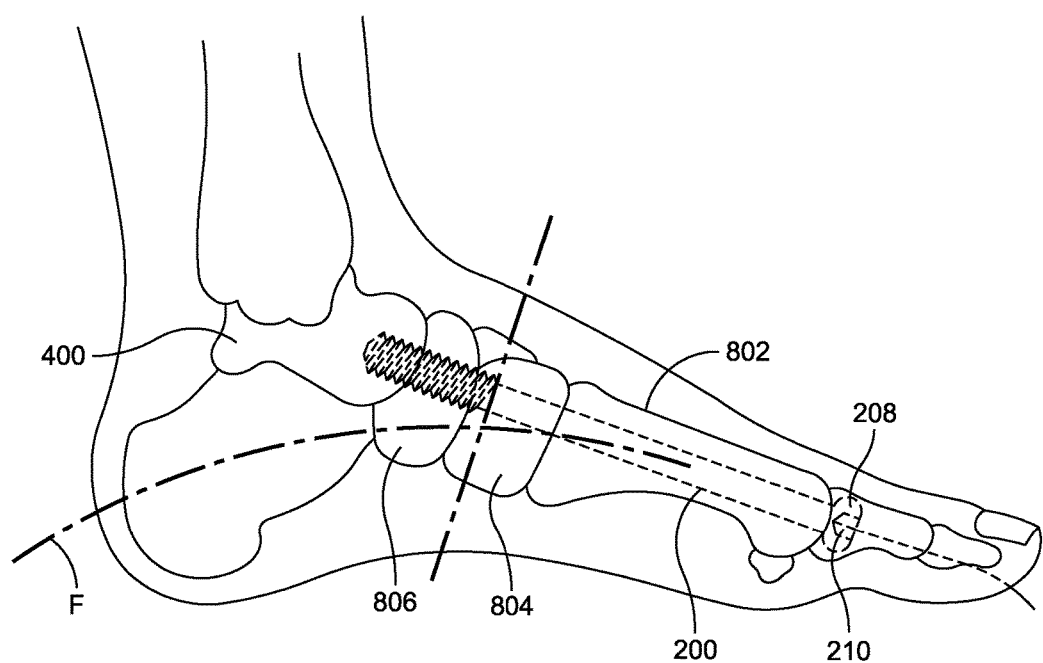
FIG. 19 illustrates a fixation device installed in the Charcot foot to repair the mid-foot arch.

As the surgeon drives bone screw 200 along an axis of metatarsal 802, bottom wall 218 of blind hole 212 of bone screw 200 contacts an end of k-wire 300 and forces the k-wire along the axis of metatarsal 802. Bone screw 200 is driven along the axis of metatarsal 802 until head 208 of the bone screw contacts a surface of metatarsal 802. FIG. 19 illustrates a bone screw 200 installed through the metatarsal 802, cuneiform 804, navicular 806, and secured in talus 400. As shown in FIG. 19, fixation devices 200 restore the arch of the mid-foot as identified by line F.

The fixation devices described herein may also be used in a variety of other surgical procedures in which the extension of a k-wire through a bone or tissue will not cause damage to an artery or tissue as will be understood by one skilled in the art. Advantageously, the fixation devices described herein provide enhanced strength over conventional hollow fixation devices along with enhanced safety as they do not include through holes enabling fluid to flow into a body of a patient. Additionally, the fixation devices disclosed herein do not require holes for the fixation devices to be drilled into bone or sealing the central hole as do conventional hollow fixation devices.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A method, comprising:
    inserting a k-wire into a bone such that a portion of the k-wire extends from a surface of the bone;
    sliding a blind hole of a fixation device over a portion of the k-wire that extends from a surface of the bone;
    driving the fixation device into the bone along an axis defined by the k-wire, a bottom wall of the blind hole contacting an end of the k-wire as the fixation device is driven into the bone; and
    removing the k-wire from the blind hole.

2. The method of claim 1, wherein the fixation device includes an elongate body extending from a distal end to a proximal end, the distal end defining the blind hole extending to a depth from a distal tip.

3. The method of claim 2, wherein the distal end includes a fluted shank extending from the distal tip.

4. The method of claim 1, further comprising:
    removing a portion of the fixation device in-situ, the removed portion of the fixation device including the blind hole.

5. A method, comprising:
    inserting a k-wire through a first bone and through a second bone such that a portion of the k-wire extends from a surface of the second bone;
    sliding a blind hole of a fixation device over the end of the k-wire;
    driving the fixation device into the second bone and the first bone along an axis defined by the k-wire, a bottom wall of the blind hole contacting the end of the k-wire as the fixation device is driven into the bone; and
    removing the k-wire from the blind hole.

6. The method of claim 5, wherein driving the fixation device includes rotating the fixation device using a driving tool.

7. The method of claim 5, wherein the first bone is a talus and the second bone is a calcaneus.

8. The method of claim 5, wherein the first bone is a tibia and the second bone is a fibula.

9. The method of claim 5, wherein the fixation device includes an elongate body extending from a distal end to a proximal end, the distal end defining the blind hole extending to a depth from a distal tip.

10. The method of claim 9, wherein the fixation device further includes a head disposed at the proximal end of the elongate body, the head having a diameter greater than an external diameter of the elongate body.

* * * * *